United States Patent
Beller et al.

(10) Patent No.: US 6,169,201 B1
(45) Date of Patent: Jan. 2, 2001

(54) PROCESS FOR THE PREPARATION OF N-ACYLAMINO ACIDS

(75) Inventors: Matthias Beller, Ismaning; Markus Eckert, Muchen; Wahed Moradi, Munich, all of (DE)

(73) Assignee: Degussa-Huels AG, Marl (DE)

( * ) Notice: Under 35 U.S.C. 154(b), the term of this patent shall be extended for 0 days.

(21) Appl. No.: 09/311,532

(22) Filed: May 13, 1999

(30) Foreign Application Priority Data

May 13, 1998 (DE) ................................. 198 21 380

(51) Int. Cl.[7] .................................................. C07C 51/08
(52) U.S. Cl. .................. 562/497; 562/408; 562/450; 562/507; 562/575; 562/406; 562/526
(58) Field of Search .................... 562/406, 408, 562/450, 497, 507, 526, 575

(56) References Cited

FOREIGN PATENT DOCUMENTS

| 3242374 | 5/1983 | (DE) . |
| 19629717 | 2/1998 | (DE) . |

OTHER PUBLICATIONS

Tetrahedron Letters, vol. 36, No. 47, 1995, pp. 8621–8624, Nakamura et al., 'Synthetic Studies on Vancomycin: Synthesis of Seco–Aglucovancomycins.'*

European Search Report, dated Aug. 27, 1999.

* cited by examiner

*Primary Examiner*—Johann Richter
*Assistant Examiner*—Brian J. Davis
(74) *Attorney, Agent, or Firm*—Selitto & Associates

(57) ABSTRACT

Process for the preparation of N-acetyl protected amino acids of Formula I

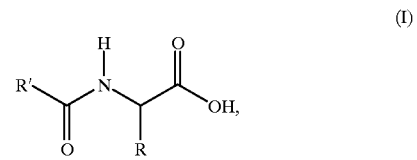

by amido carbonylation utilizing carbon monoxide, nitrile, and an aldehyde in the presence of a metal catalyst.

18 Claims, No Drawings

PROCESS FOR THE PREPARATION OF N-ACYLAMINO ACIDS

FIELD OF THE INVENTION

The invention is directed to a process for the preparation of N-acylamino acids of the general Formula I

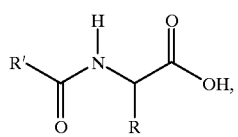

R is hydrogen, a carboxyl group, a $(C_1-C_{12})$-alkyl group, which may be saturated, straight chain, branched or cyclic, a $(C_2-C_{12})$-alkenyl residue, which may be mono- or polyunsaturated, straight chain, branch chain, or cyclic and a $(C_1-C_8)$-acyloxy group, as well as a $(C_5-C_{18})$-aryl residue.

R' is hydrogen, a saturated straight chain, branch chain or cyclic $(C_2-C_{14})$alkenyl residue, a $(C_6-C_{18})$-alkyl-$(C_5-C_{18})$-aryl residue or a poly-unsaturated $(C_2-C_{10})$-alkenyl-$(C_5-C_{18})$ residue.

DESCRIPTION OF THE PRIOR ART

N-acyl amino acids are important starting materials in the synthesis of peptides as well as intermediates for the preparation of bioactive materials. Furthermore, they find use as detergents, drilling additives and food additives.

It is known to produce N-acyl amino acids through the acylation of corresponding amino acids with the occurrence of salt by-products. In the case of non-natural amino acids, the corresponding amino acid must frequently be produced beforehand involving several steps. A one-step process which avoids the disadvantages is the amido carbonylation of aldehydes and amides which is set forth in the following reaction scheme.

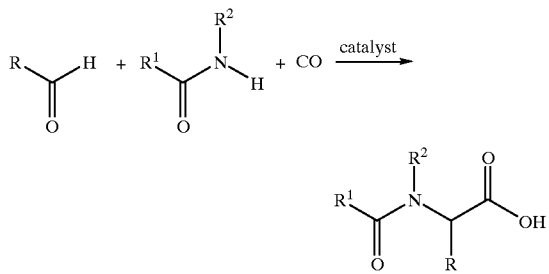

Amido carbonylation was first described by Wakamatsu, et al., (Chemical Communications 1971, page 1540 and in DE-A2-21 15 985). The carbonylation is carried out in the presence of hydrogen in the molecular ratio of CO: $H_2$=3:1. As catalyst, there is utilized the cobalt carbonyl complex $CO_2(CO)_8$, which is used in a concentration of 30 mmol of Co-metal per liter of reaction mixture.

A further cobalt catalyzed procedure based on amido carbonylation is described in British patent 2,252,770. Therein the synthesis of n-acylamino acids is carried out by reaction of a carboxylic acid amid with an aldehyde and carbon monoxide in the presence of a metal catalyst and an acid as cocatalyst.

European Publication EP-B-0 338 330 describes a procedure for the preparation of N-acyl glycine derivatives through the use of a catalyst system comprising a palladium compound and an ionic halide. In DE 195 45 641 and DE 196 29 717, there is described a procedure for the preparation of N-acyl glycine derivatives from carboxylic acid amides and an aldehyde under palladium catalysis. As cocatalyst, there are utilized ionic halides and additionally acid is added. The known procedures to amido carbonylation start with carboxylic acid amides. In many cases however, such carbon acid amides are not available in sufficient amounts to be obtained economically on a production scale so that the high variable costs of the carbon acid amide stand in the way of the technical scale realization of the corresponding procedures.

SUMMARY OF THE INVENTION

The purpose of the present invention therefore, is to provide an improved procedure for the production of amino acids through amide carbonylation that permits the reaction to be carried out in a cost effective manner.

The object of the present invention is a procedure for the preparation of N-acyl amino acids of Formula I

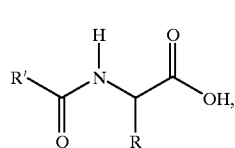

wherein

R is hydrogen, carboxyl group, a $(C_1-C_2)$-alkyl group which may be saturated, straight chain, branched or cyclic, a $(C_2-C_{12})$-alkenyl residue, which may be mono- or polyunsaturated, straight chain, branch chain, or cyclic and a $(C_1-C_8)$-acyloxy group, as well as a $(C_5-C_{18})$-aryl residue, R' is hydrogen, a saturated straight chain, branch chain or cyclic $(C_2-C_{14})$-alkenyl residue, a $(C_6-C_{18})$-alkyl-$(C_5-C_{18})$-aryl residue or a poly-unsaturated $(C_2-C_{10})$-alkenyl-$(C_5-C_{18})$ residue, which is characterized thereby that a nitrile of general Formula II

  R'CN (II), wherein R' has the value stated above, is reacted with an aldehyde of general Formula III

  R—CHO (III), in which R has the meaning above in the presence of an acid; carbon monoxide and a metal catalyst. In this way, it is possible, in highly cost efficient ways, to produce the desired compounds of general Formula I. Nitriles form the precursors of the appropriate carboxylic acid amides in virtually every case, whereby their lower price may be achieved.

DISCUSSION OF THE PREFERRED EMBODIMENTS

In accordance with the present invention any nitrile may be utilized. Examples of suitable nitrites include acetonitrile, benzonitrile, substituted benzonitriles, benzyl cyanide, acrylonitrile, malondinitrile, adiponitrile, butyl cyanide, allylcyanide, mandelo cyano nitrile and fatty acid nitriles.

With respect to the procedures of the present invention, any desired aldehydes can be used: formaldehyde, acetaldehyde, propionaldehyde, butyraldehyde, valeraldeyde, 2-ethyl hexanol, isobutryaldehyde, furfural, crotonaldehyde, acrolein, benzaldehyde, substituted benzaldehyde phenyl-acetaldehyde, 2,4-dihydroxyphenyl acetaldehyde, glyoxalic acid and α-acetoxy propionaldehyde. One may also utilize dialdehyde compounds. Also suitable are aldehyde oligomers such as paraformaldehyde, acetals, allyl alcohols and epoxides, substances which can form an aldehyde under the given reaction conditions.

The aldehydes can be provided to the reaction in the form of their trimers or oligomers. As acids, there may, in principle, be used all compounds which are suitable for the nitrile hydrolyses in question. It is preferred to utilize acids having a $pK_a$ value of <4. Preferably, sulfuric acid or a hydrogen halide such as hydrogen chloride or hydrogen bromide is utilized in this reaction.

One may also use acid mixtures of such acids. As an especially preferred modification there may be utilized a mixture of a strong acid such as sulfuric acid or hydrogen bromide in the presence of formic acid. The formic acid may be utilized in a range of 1–100 equivalents relative to the nitrile.

As active metal catalyst all those catalysts known to those skilled in the art may, in principle, be utilized for the reaction in question. Preferred are metal catalysts of palladium-(O) as well as cobalt-(O) compounds. As cobalt catalysts, suitably precatalysts, there are preferably used cobalt carbonyls for example solid $CO_2(CO_8)$. The cobalt carbonyl may be formed in situ from the known cobalt (II) and cobalt (III) compounds such as for example cobalt (II) acetate, cobalt (II) chloride, or cobalt (II) bromide in the presence of carbon monoxide if necessary, under the addition of $H_2$. As palladium catalysts as well as precatalysts, any palladium (II) compound, palladium-O compound and palladium on carrier materials, such as palladium on activated charcoal, may be utilized. As examples of palladium (II) compounds are palladium acetate, palladium halides, palladium nitriles, palladium nitrates, palladium carbonates, palladium ketonates, palladium acetyl acetonates, as well as allyl palladium complexes. Particularly preferred members of the group are $PdBr_2$, $PdCl_2$, $LiAc_2PdBr_4$, $Li_2PdCl_4$, and $Pd(OAc)_2$. Examples of palladium-O compounds are palladium phosphine complexes and palladium olefin complexes. Particularly preferred representatives are palladium (dba) complexes (dba=dibenzylidene acetone) and $Pd(PPh_3)_4$.

As particularly valuable members of the palladium phosphine complex group, there may be mentioned bisphosphine palladium (II) compounds. The complexes can be added as such or generated in a reaction mixture of a palladium (II) compound such as for example $PdBr_2$, $PdCl_2$, or palladium (II) acetate under the addition of phosphines such as triphenyl phosphine, tritolyl phosphine, bis-(diphenylphosphino) ethane, 1,4-bis-(diphenylphos-phino) butane or 1,3-bis-(diphenylphosphinol)propane.

Of the mentioned palladium phosphine complexes bis-triphenyl phosphine palladium (II) bromide-$PdBr_2(PPh_3)_2$ and the corresponding chloride are particularly preferred. These complexes can be added as such or as a reaction mixture obtained from palladium (II) bromide or chloride and triphenyl phosphine.

The process in accordance with the present invention may be carried out in the presence of between 0.0001 to 5 mol % of palladium compound (calculated as palladium metal), suitably from 0.001–4 mol % and particularly preferred from 0.01–2 mol % based on nitrile is sufficient. (The ratio is that of palladium metal relative to the amount of nitrile).

As halogen halides, there may be utilized for example, phosphonium bromides and phosphonium iodides, for example tetrabutyl phosphonium bromide or tetrabutyl phosphonium iodide, as well as ammonium-, lithium-, sodium-, and potassium chloride, bromide, and iodide. The preferred halides are chloride and bromide. Suitably the ionic halide is utilized in amounts of from 1 to 100 mol %, suitably 2–40 mol % and particularly preferred 5–30 mol % relative to the nitrile.

As solvents any of the solvents generally known to one skilled in the art can, in principle, be utilized. Preferred are dipolar aprotic compounds. Examples thereof are dioxane, tetrahydrofuran, N-methylpyrrolidone, ethylene glycol dimethyl ether, acetic acid ethyl ester, acetic acid, acetonitrile, benzonitrile, tertbutylmethyl ether, dibutyl ether, sulfolan, N,N-dimethyl acetamide or mixtures thereof. The solvents can be utilized in pure form containing products as well as saturated with the products. As solvents, there are preferred n-methyl pyrrolidone, dimethyl formamide and acetonitrile.

The reaction can take place at pressures between 1–250 bar, preferably from 10 to 150 bar at temperatures in the range of 0–200° C., preferably from of 50–150° C.

The process of the present invention can be carried out as a single container procedures or preferably in two steps. In the two-step process, the nitrile is added dropwise to a mixture of water and an acid, for example concentrated sulfuric acid. After addition of solvent, aldehyde, cobalt or palladium catalyst and ionic halide, the mixture is reacted with carbon monoxide. For the entire procedure, there are isolated yields of up to 99% of N-acylamino acid.

If desired, the process may be carried out in a single step. Therein for example, one dissolves the aldehyde, the palladium compound and the halide in the nitrile and drips this mixture into the acid water mixture and treats this in the presence of carbon monoxide to yield the end product.

It is furthermore possible, by chiral modification of the metal catalyst to readily obtain access to enantiomer enriched N-acyl amino acids.

By the term $C_5$–$C_{18}$-aryl residue, one understands to mean, for example (if required substituted) phenyl-, naphthyl-, anthryl-, phenanthryl-, biphenyl residue or a 5,6 or 7-membered hetero aromatic compound, for example with nitrogen, oxygen, or sulfur in the ring, whereby these residues may be substituted with fluorine, chlorine, bromine, iodine, or OH, $NO_2$, CN, $CO_2H$. CHO, $SO_3R"$, $SO_2R"$, SOR", NHCOR", COR", NHCHO, COAr, $CO_3Ar$, $CF_3$, $CONH_2$, $CHCHCO_2R"$, SiR", $POAr_2$, POR".

Under a ($C_1$–$C_{12}$)-alkyl residue, one understands to mean an alkyl residue with 1–12 carbon atoms in which all combination of isomers which are possible for such a residue are included. This may be also include carbocycles. Correspondingly also for the ($C_2$–$C_{26}$) alkyl residues. By ($C_2$–$C_{12}$) alkylene residues is understood alkenyl residue having 1–12 carbon atoms, wherein all possible isomeric combinations for such a residue are possible. This may also exist as a carbocycle. This also applies to the $C_2$–$C_{24}$) alkenyl residue. By the term ($C_1$–$C_8$) alkoxy residue, one understands to mean a linear or branched alkyl group having up to 8 carbon atoms, including all possible isomeric binding combinations for this residue which is bound to the molecule via a carbonyloxy function.

The alkyl and alkenyl groups carrying in the residues R and R' may be substituted by fluorine, chlorine, bromine, iodine, or OH, $NO_2$, CN, $CO_2H$, CHO, $SO_3R"$, $SO_2R"$, SOR", NHCOR", COR", NHCHO, COAr, $CO_3Ar$, $CF_3$, $CONH_2$, $CHCHCO_2R"$, SiR", $POAr_2$, POR".

The abbreviation Ar stands for a ($C_5$–$C_{18}$)-aryl residue. R" means a ($C_1$–$C_{12}$)-alkyl residue that is saturated, straight chain or branch chain or may exist in a cyclic form. ($C_1$–$C_{12}$)-alkenyl reside is mono or polyunsaturated straight chain, branch chain or in cyclic form.

Until the present invention, an in situ of preparation of carboxylic acid amides from carboxylic nitriles for purposes amido carbonylation has never been suggested. This, among other things, may be attributed thereto that a selective preparation of carbon acid amides from nitriles under amido carbonylation additions is principally problematic. On the basis of the fact that in amido carbonylation the amount of water set free in the first step led to the expectation that at higher acid concentrations, the not-yet converted carboxylic acid amide would be hydrolyzed to the carboxylic acid and thereby a substantial reduction of yield would occur. Furthermore, it would be expected that the amounts of acid necessary for the rapid hydrolysis for the nitrile would lead to an increase in the side reactions between the carbon acid amides and the aldehydes which would negatively affect the level of activity and life span of the metal catalyst.

EXAMPLES

The following examples should be considered as exemplary and not limiting of the present invention.

Example 1

1.1 g acetonitrile were dripped with stirring into a mixture of 1.5 g sulfuric acid and 0.5 g of water and subsequently reacted with 25 ml N-methyl pyrrolidone with 2.8 g cyclo hexyl carbaldehyde, 0.05 g bis(triphenyl phosphine)-palladium (II) bromide and 0.76 g lithium bromide in a 300 ml autoclave under 60 bar carbon monoxide pressure at 120° C. After reaction time of 12 hours the mixture was analyzed under high pressure liquid chromatography. There was found 4.6 g N-acetyl cyclohexyl glycine which corresponds to a yield of 92%.

Example 2

1.6 g of benzonitrile were dripped under stirring to a mixture of 2.5 g sulfuric acid and 0.5 g water and subsequently reacted in 25 ml of N-methyl pyrrolidone with 2.8 g cyclohexyl carbaldehyde, 0.266 g palladium on active charcoal (10%) and 0.76 g lithium bromide in a 300 ml autoclave at 120° C. with carbon monoxide pressure at 60 bar. After reaction time of 12 hours the mixture was analyzed under high pressure liquid chromatography. Those shows 4.58 g in N-benzoyl cyclohexyl glycine which corresponds to a yield of 17%.

Example 3

In an autoclave containing a solution of 2.8 g of cyclohexyl carbaldehyde, 0.05 g bis(triphenyl phosphine) palladium (II) bromide and 1.5 g tetrabutyl ammonium bromide in 25 ml of acetonitrile were added under stirring to a mixture of 2.5 g sulfuric acid and 0.5 g water; thereafter pressurized to 60 bar of carbon monoxide and heated to 120° C. After reaction time of f 12 hours, the mixture was analyzed by high pressure liquid chromatography. This shows 1.6 g N-acetyl cyclohexyl glycine corresponding to a yield of 32%.

Examples 4–9

In analogy to Example 1, the following N-acyl amino acids were produced (Table 1):

| Example | $R^1$ | R | Catalyst | Yield [%] |
|---|---|---|---|---|
| 4 | $CH_3$— | 4-MeO-C₆H₄— | $PdBr_2/2PPh_3$ | 76 |
| 5 | $CH_3$— | 3-MeO-C₆H₄— | $PdBr_2/2PPh_3$ | 61 |
| 6 | $CH_3$— | 2-MeO-C₆H₄— | $PdBr_2/2PPh_3$ | 65 |
| 7 | $C_6H_5$—$CH_2$— | cyclohexyl— | $PdBr_2/2PPh_3$ | 43 |
| 8 | $CH_3$— | 1-naphthyl— | $PdBr_2/2PPh_3$ | 54 |
| 9 | $CH_3$— | 2,4,4-trimethylpentyl— | $PdBr_2/2PPh_3$ | 82 |

Example 10

25 g acetonitrile were stirred with 1.2 g formic acid and 0.8 g hydrogen bromide (in glacial acetic acid) for 2 hours at room temperature and subsequently reacted with 2.8 g cyclohexyl carbaldehyde, 0.05 g bis(triphenyl phosphine)-palladium (II) dibromide in a 300 ml autoclave at 100° C. under 60 bar pressure of carbon monoxide. After 12 hours reaction time the mixture is analyzed by high pressure liquid chromatography. This shows a yield of 1.5 g N-acetyl cyclohexyl glycine in a yield of 30%.

Example 11

25 g acetonitrile in 1.2 g formic acid and 1.5 g tetrabutyl ammonium bromide, 0.5 g sulfuric acid, 2.8 g cyclohexyl carbaldehyde and 0.05 g bis(triphenyl phosphine)-palladium (II) dibromide for 2 hours at room temperature and subsequently reacted at 100° C. in a 300 ml autoclave under carbon dioxide at 60 bar pressure. After 12 hours of reaction tie, the mixture is analyzed for high pressure liquid chromatography. This shows a yield of 1.1 g N-acetyl cyclohexyl glycine in a yield of 22%.

What is claimed is:
1. A process for the preparation of N-acylamino acids of the Formula I

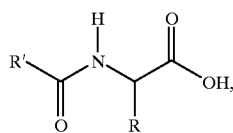

(I)

wherein R is hydrogen, a carboxyl group, a $(C_1–C_{12})$-alkyl group which may be saturated, which may be, straight chain, branched or cyclic, a $(C_2–C_{12})$-alkenyl group which may be mono- or polyunsaturated, straight chain, branched chain, or cyclic and a $(C_1–C_8)$-acyloxy group, as well as a $(C_5–C_{18})$-aryl residue, R' is hydrogen, a saturated straight chain, branch chain or cyclic $(C_2–C_{14})$-alkenyl residue, a $(C_6–C_{18})$-alkyl-$(C_5–C_{18})$-aryl residue or a polyunsaturated $(C_2–C_{10})$-alkenyl-$(C_5–C_{18})$ residue, which comprises reacting a compound of Formula II

R'CN    (II),

R' has the value stated above with an aldehyde of general Formula III

R—CHO    (III), in which R has the meaning above in the presence of an acid, carbon monoxide and a metal catalyst.

2. The process in accordance with claim 1 wherein the aldehyde is in the form of a trimer or oligomer.

3. The process in accordance with claim 1 comprising carrying out the reaction in the presence of an acid having a $pK_a$ value of less than 4.

4. The process in accordance with claim 3 wherein the acid is sulfuric acid or a hydrogen halide.

5. Process in accordance with claim 4 comprising adding formic acid to the reaction mixture.

6. The process in accordance with claim 1 comprising the use of an active metal catalyst selected from the group consisting of a palladium-(O) compound or a cobalt-(O) compound.

7. A process according to claim 6 wherein the amount of palladium compound is 0.0001 to 5 mol % relative to the amount of nitrile utilized.

8. A process in accordance with claim 7 wherein the amount of palladium compound is between 0.01 and 2 mol % relative to the nitrile.

9. A process in accordance with claim 1 wherein the reaction is carried out in the presence of a halogen salt.

10. A process in accordance with claim 9 wherein the halogen salt is utilized in a concentration of between 0.01 to 100 mol % relative to the nitrile.

11. A process in accordance with claim 1 wherein the reaction is carried out in a dipolar aprotic solvent or mixture of such solvents.

12. A process in accordance with claim 11 wherein the solvent is selected from the group consisting of N-methyl pyrrolidine, dimethyl formamide and acetonitrile.

13. A process in accordance with claim 1 wherein the reaction is carried out in the presence of carbon monoxide at a pressure of between 1 and 250 bar.

14. A process in accordance with claim 13 wherein the carbon monoxide pressure is between 10 and 150 bar.

15. A process in accordance with claim 1 wherein the reaction is carried out in a temperature range of between 0 to 200° C.

16. A process in accordance with claim 15 wherein the reaction is carried out in a temperature range of 50 to 150° C.

17. A process in accordance with claim 1, wherein the nitrile is added to the acid and thereafter the solvent aldehyde, metal catalyst, and an anionic halide is added to said aqueous acid to form an acid mixture and, reacting said acid mixture with carbon monoxide.

18. A process in accordance with claim 1, wherein the aldehyde, the metal catalyst, and an anionic halide are dissolved in the nitrile, and said nitrile solution added to aqueous acid, the thus formed solution is then reacted with carbon monoxide.

* * * * *